(12) United States Patent
Moon

(10) Patent No.: US 10,335,264 B2
(45) Date of Patent: Jul. 2, 2019

(54) VASCULAR GRAFT

(71) Applicant: Byung Choo Moon, Toronto (CA)

(72) Inventor: Byung Choo Moon, Toronto (CA)

(73) Assignee: Byung Choo Moon, Toronto, Ontario (CA)

( * ) Notice: Subject to any disclaimer, the term of this patent is extended or adjusted under 35 U.S.C. 154(b) by 0 days.

(21) Appl. No.: 15/455,314

(22) Filed: Mar. 10, 2017

(65) Prior Publication Data

US 2018/0256310 A1  Sep. 13, 2018

(51) Int. Cl.
*A61F 2/07* (2013.01)
*A61F 2/06* (2013.01)

(52) U.S. Cl.
CPC ............... *A61F 2/06* (2013.01); *A61F 2/064* (2013.01); *A61F 2002/065* (2013.01); *A61F 2210/0076* (2013.01); *A61F 2220/0075* (2013.01); *A61F 2230/0069* (2013.01)

(58) Field of Classification Search
CPC ...... A61F 2/07; A61F 2/82; A61F 2/91; A61F 2/95; A61F 2/06
USPC ................................................ 623/1.15–1.48
See application file for complete search history.

(56) References Cited

U.S. PATENT DOCUMENTS

| 6,010,529 | A | * | 1/2000 | Herweck | A61F 2/06 600/36 |
| 6,053,943 | A | * | 4/2000 | Edwin | A61F 2/07 600/36 |
| 6,165,210 | A | * | 12/2000 | Lau | A61F 2/88 623/1.12 |
| 6,270,523 | B1 | * | 8/2001 | Herweck | A61F 2/06 606/191 |
| 6,364,903 | B2 | * | 4/2002 | Tseng | A61F 2/07 427/2.24 |
| 8,647,458 | B2 | * | 2/2014 | Banas | A61F 2/86 156/184 |
| 9,763,812 | B2 | * | 9/2017 | Enzmann | A61F 2/07 |
| 2001/0021870 | A1 | * | 9/2001 | Edwin | A61F 2/06 623/1.13 |
| 2005/0131515 | A1 | * | 6/2005 | Cully | A61F 2/07 623/1.13 |
| 2009/0294035 | A1 | * | 12/2009 | Layne | A61F 2/07 156/211 |
| 2011/0093058 | A1 | * | 4/2011 | Vardi | A61F 2/07 623/1.15 |
| 2012/0330402 | A1 | * | 12/2012 | Vad | A61F 2/07 623/1.13 |
| 2013/0060327 | A1 | * | 3/2013 | Shokoohi | A61F 2/856 623/1.42 |
| 2014/0141152 | A1 | * | 5/2014 | Sostek | A61F 2/04 427/2.24 |

* cited by examiner

*Primary Examiner* — Suzette J Gherbi
(74) *Attorney, Agent, or Firm* — White and Williams LLP

(57) ABSTRACT

Provided is an artificial blood vessel including a cylindrical inner tube having a hollow part formed therein; an outer tube provided at an outer circumferential surface of the inner tube and surrounding the inner tube so as to form a double tube structure with the inner tube; and a connecting line formed in circumferential directions of the inner tube and the outer tube to connect the inner tube and the outer tube.

3 Claims, 5 Drawing Sheets

VASCULAR GRAFT

BACKGROUND

Field of the Invention

The present invention relates to an artificial blood vessel.

Discussion of Related Art

A vascular occlusive disease, generated when a blood vessel is narrowed or almost blocked due to lack of exercise and dietary habits, has been increasing year by year.

In particular, typical examples of cardiac disorders are coronary artery disease and peripheral vascular disease caused by ischemia that occurs when a blood vessel supplying nutrition and oxygen to the heart is blocked.

As a method for treating a blocked blood vessel or a substantially blocked blood vessel, a surgical method has been often chosen. As a method generally adopted as the surgical method, there is a method that tries to solve a problem of narrowness by cutting a problematic portion of a blood vessel and inserting and connecting an artificial blood vessel.

An artificial blood vessel 10 illustrated in FIG. 1 is a typical example used in the method, wherein the artificial blood vessel 10 has been developed as an alternate means for guiding the flow of blood when a blood vessel of a patient is narrowed by some factor or a function of the blood vessel is remarkably degraded.

The prior art artificial blood vessel 10 includes a tube 11 having a hollow part through which blood flows, and is formed as a single tube in which a pleat 12 is formed in the tube 11.

However, in an anastomosis between the artificial blood vessel 10 and a blood vessel near an organ in which periodical beating is generated such as the heart, it is extremely difficult to perform manual suturing. Particularly, the longer the surgery time, the more difficulties the surgery has, and there is a problem in which risk of causing complications is increased when the surgery time is too long. Particularly, suturing should be quickly completed to prevent a lot of blood from leaking when applied to the aorta.

Therefore, an artificial blood vessel, capable of being safely and quickly applied to a surgical site when surgery in which insertion of an artificial blood vessel is performed, is required.

SUMMARY OF THE INVENTION

The present invention is directed to provide an artificial blood vessel capable of being safely and quickly applied at the time of blood vessel replacement surgery.

An artificial blood vessel may include a cylindrical inner tube having a hollow part formed therein, an outer tube provided at an outer circumferential surface of the inner tube and surrounding the inner tube so as to form a double tube structure with the inner tube and a connecting line formed in circumferential directions of the inner tube and the outer tube to connect the inner tube and the outer tube.

The artificial blood vessel according to the present invention is formed in a double tube structure to quickly and safely allow the performance of blood vessel replacement surgery.

Particularly, when acute aortic dissection surgery or thoracic and abdominal aortic aneurysm surgery is performed, the artificial blood vessel can quickly and safely be used to perform a complicated process of strengthening a cut portion of the aorta and anastomosing the artificial blood vessel 10.

BRIEF DESCRIPTION OF THE DRAWINGS

The above mentioned content and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
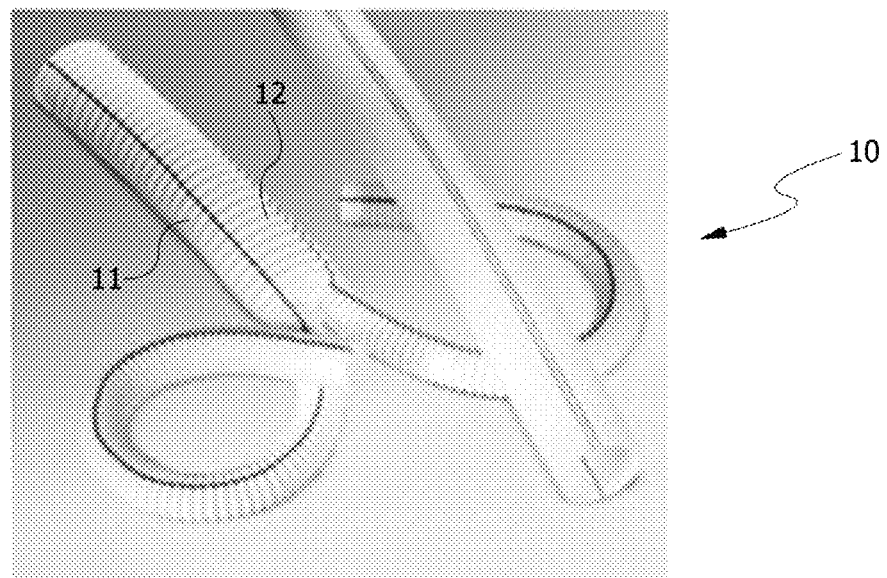
FIG. 1 is a view illustrating a prior art artificial blood vessel.

The present invention relates to an artificial blood vessel capable of being quickly and safely applied at the time of blood vessel replacement surgery.

Here, the artificial blood vessel refers to an artificial internal organ, which is an artificially made artery or vein, used to replace a damaged blood vessel in the body and connect the flow of blood, which is.

The artificial blood vessel of the present invention includes a cylindrical inner tube having a hollow hole formed therein; an outer tube provided at an outer circumferential surface of the inner tube and surrounding the inner tube to have a double tube structure with the inner tube; and a connecting line formed in a circumferential direction of the inner tube and outer tube and connecting the inner tube with the outer tube.

Here, the connection refers to bonding the inner tube and the outer tube.

In this case, a plurality of connecting lines are included, and the connecting lines may be formed at regular intervals in axial directions of the inner tube and outer tube.

In addition, the inner tube may include at least a first guide line in the axial direction, and the outer tube may include at least a second guide line in the axial direction. Particularly, the position of the second guide line corresponds to that of the first guide line.

The first guide line and the second guide line prevent the artificial blood vessel of the present invention from being twisted, and may be a marking means for marking a position of suturing of the blood vessel.

Also, the inner tube and the outer tube of the artificial blood vessel of the present invention may be formed of pleated tubes and may include at least a branched tube to be branched.

Meanwhile, the artificial blood vessel is formed of a biocompatible material or formed of at least one selected from a group consisting of nylon, silk, polytetrafluoroethylene (PTFE), polypropylene (PP), polyurethane (PU), polyethylene terephthalate (PET), a polyamide (PA), polyacrylonitrile (PAN), polyethylene (PE), polyester (PES), polyvinyl chloride (PVC), polyvinylidene fluoride (PVDF), polysiloxane (silicone rubber), polyvinyl alcohol (PVA), and polyglycolic (PGA) and polylactic acid (PLA).

Hereafter, exemplary embodiments of the present invention will be described with reference to the accompanying drawings. Terms and words used in this specification and claims should not be interpreted as limited to commonly used meanings or meanings in dictionaries and should be interpreted with meanings and concepts which are consistent with the technological scope of the invention based on the principle that the inventors have appropriately defined concepts of terms in order to describe the invention in the best way.

Therefore, since the embodiments described in this specification and configurations illustrated in drawings are only exemplary embodiments and do not represent the overall technological scope of the invention, it is understood that the invention covers various equivalents, modifications, and substitutions at the time of filing of this application.

Figure 2:
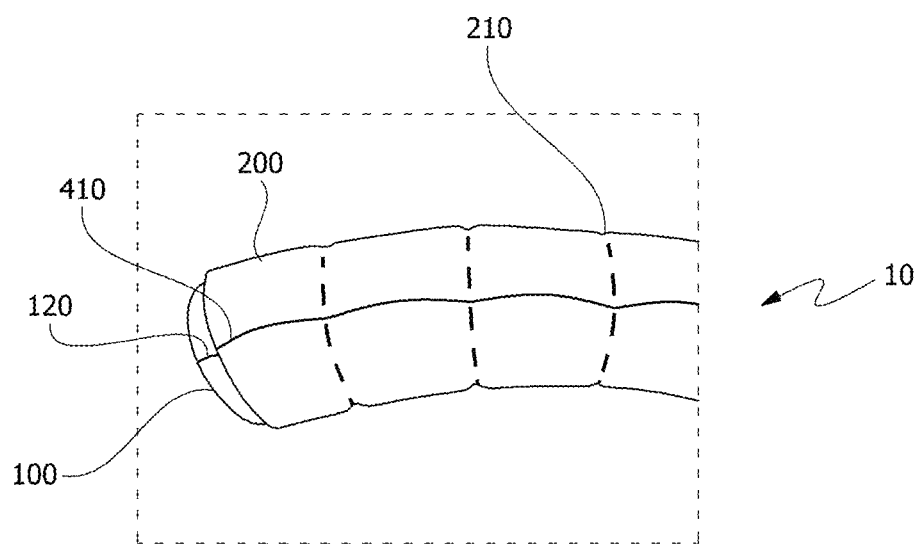
FIG. 2 is a schematic diagram of an artificial blood vessel according to an embodiment of the present invention.
Figure 3:
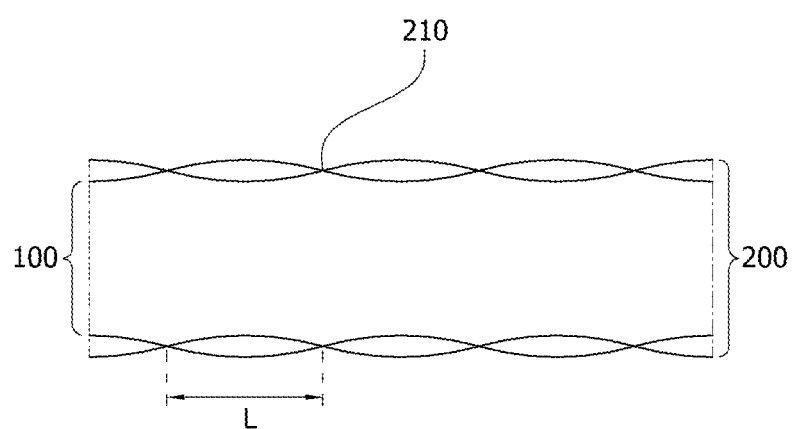
FIG. 3 is a cross-sectional view of the artificial blood vessel according to the embodiment of the present invention.
Figure 4:
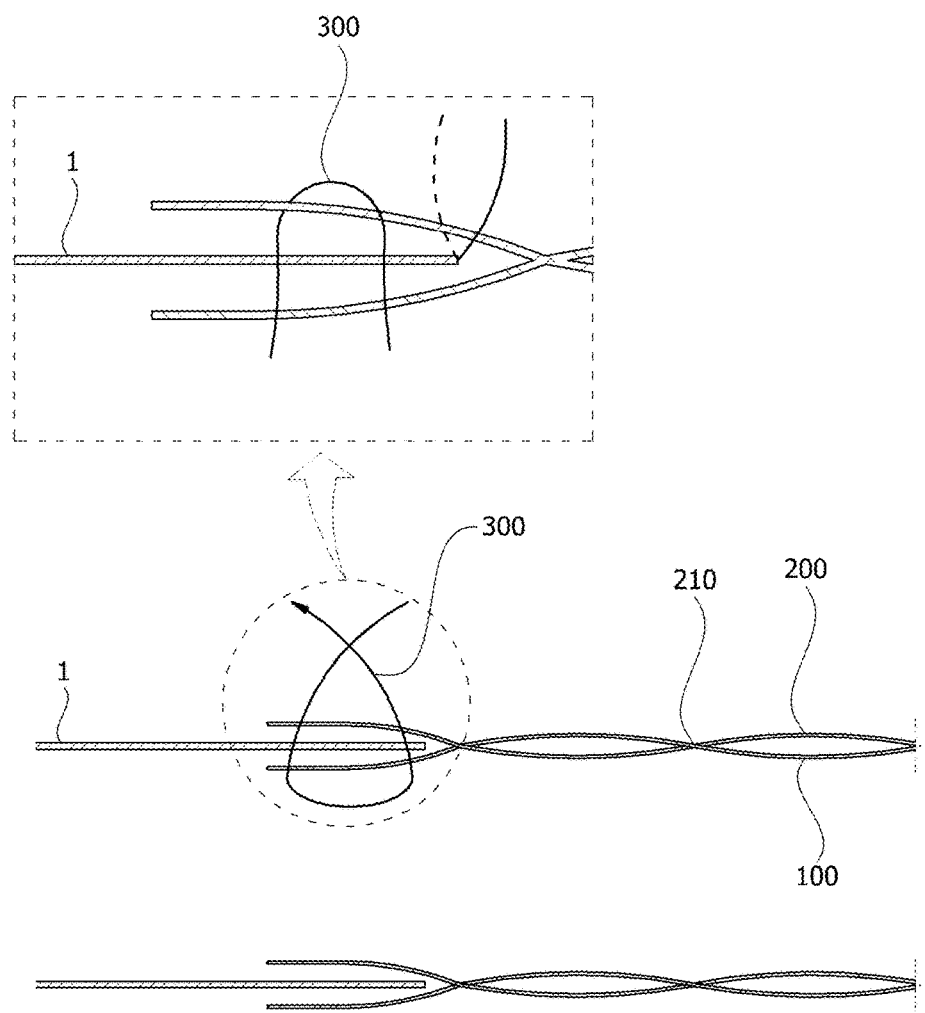
FIG. 4 is a view illustrating a process for anastomosing the artificial blood vessel according to the embodiment of the present invention with a blood vessel.
Figure 5:
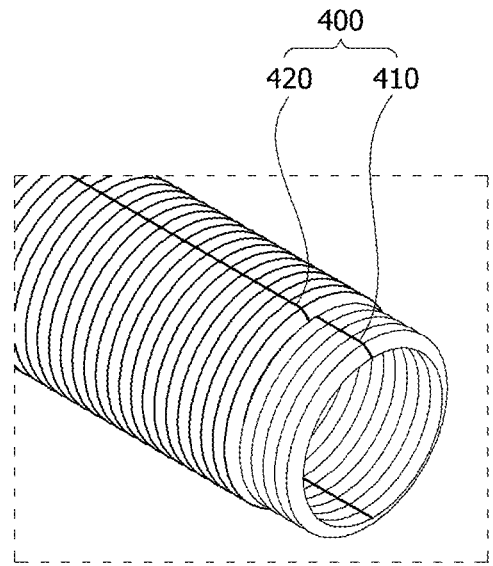
FIG. 5 is a view illustrating a portion of the artificial blood vessel according to the embodiment of the present invention.
Figure 6:
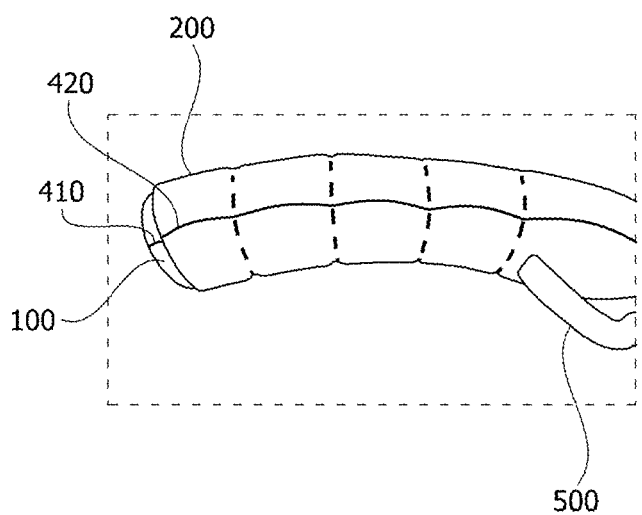
FIG. 6 is a schematic diagram of the artificial blood vessel according to another embodiment of the present invention.
Figure 7:
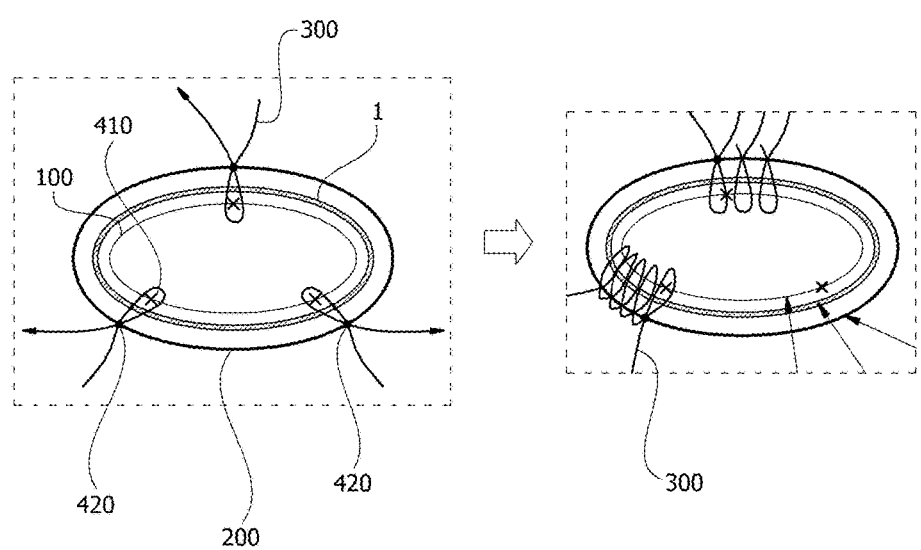
FIG. 7 is a cross-sectional view illustrating a process of anastomosing the artificial blood vessel with the blood vessel according to the embodiment of the present invention.

FIG. 2 is a schematic diagram of an artificial blood vessel according to an embodiment of the present invention, FIG. 3 is a cross-sectional view of the artificial blood vessel according to the embodiment of the present invention, FIG. 4 is a view illustrating a process for anastomosing the artificial blood vessel according to the embodiment of the present invention with a blood vessel, FIG. 5 is a view illustrating a portion of the artificial blood vessel according to the embodiment of the present invention, FIG. 6 is a schematic diagram of the artificial blood vessel according another embodiment of the present invention, and FIG. 7 is a cross-sectional view illustrating a process of anastomosing the artificial blood vessel with the blood vessel according to the embodiment of the present invention.

Hereafter, the artificial blood vessel of the present invention will be described in detail with reference to FIGS. 2 to 7 and exemplary embodiments.

The present invention relates to the artificial blood vessel 10 capable of being quickly and safely applied at the time of an artificial blood vessel replacement surgery.

Here, the artificial blood vessel 10 refers to an artificial internal organ, which is an artificially made artery or vein, used to replace a damaged blood vessel in the body and connect the flow of blood.

The artificial blood vessel 10 of the present invention may be applied to all kinds of damaged blood vessels, such as arteries, veins, and capillaries, and particularly, the artificial blood vessel 10 of the present invention may be used to strengthen a cut portion of the aorta at the time of acute aortic dissection or thoracic and abdominal aortic aneurysm surgery.

According to the illustration in FIGS. 2 and 3, the artificial blood vessel 10 of the present invention has a double tube structure formed of a cylindrical inner tube 100 and an outer tube 200.

More specifically, the artificial blood vessel 10 includes the cylindrical inner tube 100 having a hollow part formed therein; the outer tube 200 provided at an outer circumferential surface of the inner tube 100 to surround the inner tube 100, and a connecting line 210 formed in a circumferential direction to connect the inner tube 100 and the outer tube 200.

From a specific aspect, the artificial blood vessel 10 may have a roughly circular cross-sectional structure, and may be a large-diameter blood vessel such as an artery and vein of a human body or a small-diameter blood vessel such as a capillary. Further, the artificial blood vessel 10 may be formed in a structure having an outer cortical layer formed in the order of the tunica interna, the tunica media, the tunica externa with respect to the inner hollow part such as in a natural blood vessel, but, in consideration of the artificial blood vessel 10, there is no need to limit a shape if a function and the shape and of the outer tube 200 are similar to those of a natural blood vessel.

Here, the connecting line 210 of the present invention for binding the inner tube 100 and the outer tube 200 of the present invention may be composed so that the inner tube 100 and the outer tube 200 are sutured. From a specific aspect, the inner tube 100 and the outer tube 200 may be bonded by an adhesive.

Additionally, since the inner tube 100 and the outer tube 200 are partially bound rather than entirely bound, a gap may be formed between the inner tube 100 and the outer tube 200, which is a portion in which a connecting unit is not formed.

More specifically, a plurality of connecting lines 210 in a ring shape may be included in a circumferential direction of the artificial blood vessel, and the connecting lines 210 may be formed at regular intervals in axial directions of the inner tube 100 and the outer tube 200.

Here, the axial direction refers to a direction extended in a longitudinal direction of the artificial blood vessel, and particularly, may refer to a direction parallel to a major axis of the inner tube and the outer tube.

From a specific aspect, the connecting line 210 of the present invention may minimize the leakage of blood at the time of blood vessel anastomosis surgery with the artificial blood vessel 10.

According to the illustration in FIG. 4, at the time of the blood vessel anastomosis surgery, a blood vessel 1 is coupled between the inner tube 100 and the outer tube 200. More specifically, an inner diameter of the blood vessel 1 is positioned at an outer circumferential surface of the inner tube 100 in the present invention, and an outer diameter of the blood vessel 1 may be positioned at an inner circumferential surface of the outer tube 200 of the present invention. That is, a cross-sectional surface of the blood vessel 1 is positioned in the gap between the outer diameter and the inner tube 100 of the present invention, wherein the cross-sectional surface of the blood vessel 1 may be sealed by the connecting line 210. Therefore, the leakage of blood may be minimized In this case, the plurality of connecting lines 210 may be formed at an interval of 2 to 6 cm in an axial direction of the artificial blood vessel. More specifically, the connecting lines 210 on the artificial blood vessel 10 may be formed at an interval of 4 to 6 cm, for example, at an interval of 5 cm. Also, in the case of a small-diameter branched tube 500, the connecting lines 210 may be formed at an interval of 2 to 3 cm.

In addition, when the plurality of connecting lines 210 are formed at an interval of 5 cm, the user may use the artificial blood vessel 10 by cutting the artificial blood vessel 10 between the connecting lines 210. In this case, the artificial blood vessel 10 may be used by being cut at a position 2.5 cm away from the connecting line 210.

Particularly, the artificial blood vessel 10 of the present invention is segmented by the connecting line 210, and may be used by being cut into a length to be used.

Further, the artificial blood vessel 10 of the present invention includes a guide line 400. More specifically, the inner tube 100 and the outer tube 200 may include at least one guide line 400 in an axial direction, the guide line 400 formed on the inner tube 100 may be a first guide line 410, and the guide line 400 formed in the outer tube 200 may be a second guide line 420.

Here, as illustrated in FIG. 5, the first guide line 410 of the inner tube 100 and the second guide line 420 of the outer tube 200 may be formed to be opposite from each other.

The guide line 400 prevents the inner tube 100 and the outer tube 200 of the artificial blood vessel 10 from being twisted, and may be a marking means for marking the position of suturing the blood vessel 1.

As an example, three first guide lines 410 may be formed in an axial direction of the inner tube 100, and three second guide lines 420 may be formed in an axial direction of the outer tube 200.

Here, to achieve an anastomosis between the blood vessel 1 and the artificial blood vessel 10, the first guide line 410 and the second guide line 420 are positioned opposite to each other, and only a portion in which the guide line 400 is formed may be anastomosed first.

That is, after the first guide line 410 and the second guide line 420 are positioned opposite to each other, the blood vessel 1 is anastomosed using a surgical suture 300 at a portion in which the guide line 400 is formed to prevent the blood vessel 1 and the artificial blood vessel 10 from being twisted. Then, the remaining portion may be anastomosed by extending the surgical suture 300 anastomosing at the guide line 400.

Meanwhile, according to as illustrated in FIG. 6, the inner tube 100 and the outer tube 200 of the artificial blood vessel 10 of the present invention may be formed of a pleated tube, and may include at least a branched tube 500 to be branched from the artificial blood vessel 10.

In this case, although not limited thereto, for example, the branched tube 500 may be a predetermined-diameter cylindrical branched blood vessel, or may be a flare-shaped branched blood vessel in which a diameter of a portion connected with the artificial blood vessel 10 is increased. Further, the flare-shaped branched blood vessel member may be used so that blood in the artificial blood vessel 10 easily flows.

Meanwhile, the artificial blood vessel 10 is formed of a biocompatible material or formed of at least one selected from a group consisting of nylon, silk, polytetrafluoroethylene (PTFE), polypropylene (PP), polyurethane (PU), polyethylene terephthalate (PET), a polyamide (PA), polyacrylonitrile (PAN), polyethylene (PE), polyester (PES), polyvinyl chloride (PVC), polyvinylidene fluoride (PVDF), polysiloxane (silicone rubber), polyvinyl alcohol (PVA), and polyglycolic (PGA) and polylactic acid (PLA).

The artificial blood vessel 10 of the present invention is not limited thereto; however, the artificial blood vessel 10 may be the artificial blood vessel 10 for the carotid artery, iliac or femoral artery, which are middle-sized arteries, and may be the artificial blood vessel 10 for replacement of large-diameter arteries, such as the aorta. Here, a diameter of the artificial blood vessel 10 may be 10 to 45 mm, and a diameter of the branched tube 500 may be 3 to 12 mm.

Also, the artificial blood vessel 10 of the present invention may have a length of 10 to 50 cm. Although not limited thereto, the artificial blood vessel 10 may be used by being cut into a length to be used at the time of a surgery.

The detailed example for treating an aneurysm using the artificial blood vessel 10 according to the present invention will be as follows. To easily describe the present invention, a process of anastomosis between the blood vessel 1 and the artificial blood vessel 10 of the present invention will be described as an example with reference to FIG. 7.

Firstly, a surgeon cuts the artificial blood vessel 10 of the present invention into a length to be used for the surgery. Here, the operating surgeon may cut a central portion between the connecting units formed on the artificial blood vessel 10.

After that, the blood vessel 1 of a patient and the cut artificial blood vessel 10 are made to overlap. Here, the blood vessel 1 of the patient is positioned between the inner tube 100 and the outer tube 200 of the artificial blood vessel 10, and more specifically, the blood vessel 1 of the patient and the artificial blood vessel 10 are positioned to have an overlapping length of 1 to 2 cm.

Meanwhile, the first guide line 410 and the second guide line 420 formed on the inner tube 100 and in the outer tube 200 of the artificial blood vessel 10 are formed at the same position, and portions in which the guide lines 400 are formed are anastomosed using the surgical suture 300.

After only some portions in which the guide lines 400 are formed are anastomosed first, the entire portion is anastomosed, and thus the blood vessel 1 and the artificial blood vessel 10 of the present invention may be anastomosed.

Therefore, the artificial blood vessel 10 according to the present invention is formed in a double tube structure, and blood vessel replacement surgery may be quickly and safely performed.

Particularly, when acute aortic dissection surgery or thoracic and abdominal aortic aneurysm surgery is performed, the artificial blood vessel can quickly and safely perform a complicate process of strengthening a cut portion of aorta and anastomosing the artificial blood vessel 10.

While the invention has been described with reference to specific details such as detailed components, specific embodiments and drawings, these are only examples to facilitate overall understanding of the invention and the invention is not limited thereto. It will be understood by those skilled in the art that various modifications and alterations may be made.

Therefore, the spirit and scope of the invention are defined not only by the detailed description of the invention but by the appended claims, and encompasses all modifications and equivalents that fall within the scope of the appended claims.

What is claimed is:

1. An artificial blood vessel, comprising:
a cylindrical inner tube having a hollow part formed therein;
an outer tube provided at an outer circumferential surface of the inner tube and surrounding the inner tube so as to form a double tube structure with the inner tube; and
a connecting line formed in circumferential directions of the inner tube and the outer tube to connect the inner tube and the outer tube, wherein the inner tube includes at least a first guide line in an axial direction, and the outer tube includes at least a second guide line in an axial direction and is positioned at a position corresponding to a position of the first guide line.

2. An artificial blood vessel, comprising:
a cylindrical inner tube having a hollow part formed therein;
an outer tube provided at an outer circumferential surface of the inner tube and surrounding the inner tube so as to form a double tube structure with the inner tube; and
a connecting line formed in circumferential directions of the inner tube and the outer tube to connect the inner tube and the outer tube, wherein the inner tube and the outer tube are formed of a pleated tube.

3. An artificial blood vessel, comprising:
a cylindrical inner tube having a hollow part formed therein;
an outer tube provided at an outer circumferential surface of the inner tube and surrounding the inner tube so as to form a double tube structure with the inner tube; and
a connecting line formed in circumferential directions of the inner tube and the outer tube to connect the inner tube and the outer tube, wherein the artificial blood vessel includes at least a branched tube to be branched.

* * * * *